United States Patent
Eggen et al.

(10) Patent No.: US 8,659,212 B2
(45) Date of Patent: Feb. 25, 2014

(54) ULTRASOUND TRANSDUCER AND METHOD FOR MANUFACTURING AN ULTRASOUND TRANSDUCER

(75) Inventors: Trym Eggen, Horten (NO); Charles Edward Baumgartner, Niskayuna, NY (US); David A Chartrand, Phoenix, AZ (US); Bjornar Sten-Nilsen, Horten (NO); Rolf Johannessen, Horten (NO); Jessica Abraham, Phoenix, AZ (US)

(73) Assignee: General Electric Company, Schenectady, NY (US)

( * ) Notice: Subject to any disclaimer, the term of this patent is extended or adjusted under 35 U.S.C. 154(b) by 44 days.

(21) Appl. No.: 13/398,692

(22) Filed: Feb. 16, 2012

(65) Prior Publication Data
US 2013/0214641 A1 Aug. 22, 2013

(51) Int. Cl.
*H01L 41/08* (2006.01)
*A61B 8/14* (2006.01)

(52) U.S. Cl.
USPC .......................................... 310/334; 600/459

(58) Field of Classification Search
USPC .......................................... 310/334; 600/459
See application file for complete search history.

(56) References Cited

U.S. PATENT DOCUMENTS

| | | | |
|---|---|---|---|
| 6,894,425 B1 * | 5/2005 | Solomon et al. | 310/334 |
| 7,431,698 B2 | 10/2008 | Bruestle | |
| 7,451,651 B2 | 11/2008 | Woychik et al. | |
| 7,741,756 B2 | 6/2010 | Sudol | |
| 7,775,979 B2 | 8/2010 | Thomenius et al. | |
| 7,791,252 B2 * | 9/2010 | Baumgartner et al. | 310/334 |
| 7,795,784 B2 * | 9/2010 | Davidsen et al. | 310/334 |
| 7,859,170 B2 * | 12/2010 | Knowles et al. | 310/334 |
| 7,952,260 B2 | 5/2011 | Haider et al. | |
| 8,242,665 B2 * | 8/2012 | Robinson et al. | 310/334 |
| 2003/0028108 A1 * | 2/2003 | Miller | 600/437 |
| 2005/0140248 A1 * | 6/2005 | Kuniyasu et al. | 310/334 |
| 2007/0239024 A1 | 10/2007 | Eberle et al. | |
| 2010/0025785 A1 * | 2/2010 | Robinson et al. | 257/416 |
| 2010/0317972 A1 | 12/2010 | Baumgartner et al. | |
| 2011/0034809 A1 | 2/2011 | Eberle et al. | |
| 2011/0059660 A1 | 3/2011 | Konkle et al. | |
| 2011/0060225 A1 | 3/2011 | Cogan et al. | |

FOREIGN PATENT DOCUMENTS

WO WO-2011/033271 A1 * 3/2011

* cited by examiner

*Primary Examiner* — Thomas Dougherty
(74) *Attorney, Agent, or Firm* — The Small Patent Law Group; Dean D. Small

(57) ABSTRACT

An ultrasound transducer includes an array of acoustic elements, an integrated circuit, and an interposer. The interposer includes conductive elements that electrically connect the array of acoustic elements to the integrated circuit. An electrically conductive adhesive is engaged with the conductive elements of the interposer to electrically connect the interposer to at least one of the integrated circuit or the array of acoustic elements. The electrically conductive adhesive is anisotropically conductive.

15 Claims, 9 Drawing Sheets

ULTRASOUND TRANSDUCER AND METHOD FOR MANUFACTURING AN ULTRASOUND TRANSDUCER

BACKGROUND OF THE INVENTION

The subject matter disclosed herein relates generally to ultrasound systems, and more particularly to ultrasound transducers and methods for manufacturing ultrasound transducers.

Ultrasound systems typically include ultrasound scanning devices (e.g., an ultrasound transducer, all or a portion of which may be housed within a probe) that perform various ultrasound scans (e.g., imaging a body or other volume). The scanning devices include acoustic elements that transmit and receive ultrasound signals. The acoustic elements may be arranged in an array. The ultrasound signals received by the acoustic elements are used to generate an image of the body or other volume. For example, the received ultrasound signals may be used to generate an image of internal tissues of a patient, such as, but not limited to, an image of a patient's heart.

At least some known ultrasound systems include electronics (e.g., one or more integrated circuits) that perform transmit and/or receive beamforming operations on the ultrasound signals. Such beamforming electronics are electrically and mechanically connected to the acoustic elements of the ultrasound transducer for performing the beamforming operations. The electrical and mechanical connection between the beamforming electronics and the acoustic elements may be a direct connection or may be provided through an interposer that extends between the acoustic elements and the beamforming electronics.

In some known ultrasound systems, an adhesive is used to mechanically connect or both mechanically and electrically connect the beamforming electronics to the acoustic elements. But, it may be difficult or impossible to apply enough adhesive to provide the mechanical connection with a predetermined strength, for example because of a limited amount of space between adjacent electrical contacts of the beamforming electronics and the acoustic elements or because the adhesive electrically shorts adjacent electrical contacts. Accordingly, the mechanical connection provided by the adhesive may be severed, for example during operation and/or transport of the ultrasound system, which may electrically disconnect the beamforming electronics from the acoustic elements and thereby disrupt operation of the ultrasound system.

BRIEF DESCRIPTION OF THE INVENTION

In one embodiment, an ultrasound transducer includes an array of acoustic elements, an integrated circuit, and an interposer. The interposer includes conductive elements that electrically connect the array of acoustic elements to the integrated circuit. An electrically conductive adhesive is engaged with the conductive elements of the interposer to electrically connect the interposer to at least one of the integrated circuit or the array of acoustic elements. The electrically conductive adhesive is anisotropically conductive.

In another embodiment, a method is provided for manufacturing an ultrasound transducer. The method includes providing an array of acoustic elements and an integrated circuit, providing an interposer having conductive elements, electrically connecting the conductive elements of the interposer to the integrated circuit, and electrically connecting the conductive elements of the interposer to the array of acoustic elements. At least one of electrically connecting the interposer to the integrated circuit or electrically connecting the interposer to the array of acoustic elements includes applying to the interposer an electrically conductive adhesive that is anisotropically conductive such that the electrically conductive adhesive is engaged with the conductive elements of the interposer.

In another embodiment, an ultrasound transducer includes an array of acoustic elements, an integrated circuit, a first interposer comprising first conductive elements, a second interposer comprising second conductive elements, and an electrically conductive adhesive that is anisotropically conductive. The electrically conductive adhesive includes a first electrically conductive adhesive layer that is engaged with the first conductive elements of the first interposer such that the first electrically conductive adhesive layer electrically connects the first conductive elements to the acoustic elements. The electrically conductive adhesive also includes a second electrically conductive adhesive layer that is engaged with the first conductive elements of the first interposer and the second conductive elements of the second interposer such that the second electrically conductive adhesive layer electrically connects the first and second conductive elements together. A third electrically conductive adhesive layer is engaged with the second conductive elements of the second interposer such that the third electrically conductive adhesive layer electrically connects the second conductive elements to the integrated circuit.

In another embodiment, an ultrasound transducer includes an array of acoustic elements having electrical contacts, and an integrated circuit having electrical contacts. An electrically conductive adhesive is engaged with the electrical contacts of the array of acoustic elements and is engaged with the electrical contacts of the integrated circuit to electrically connect the integrated circuit to the array of acoustic elements. The electrically conductive adhesive is anisotropically conductive.

DETAILED DESCRIPTION OF THE INVENTION

Figure 1:
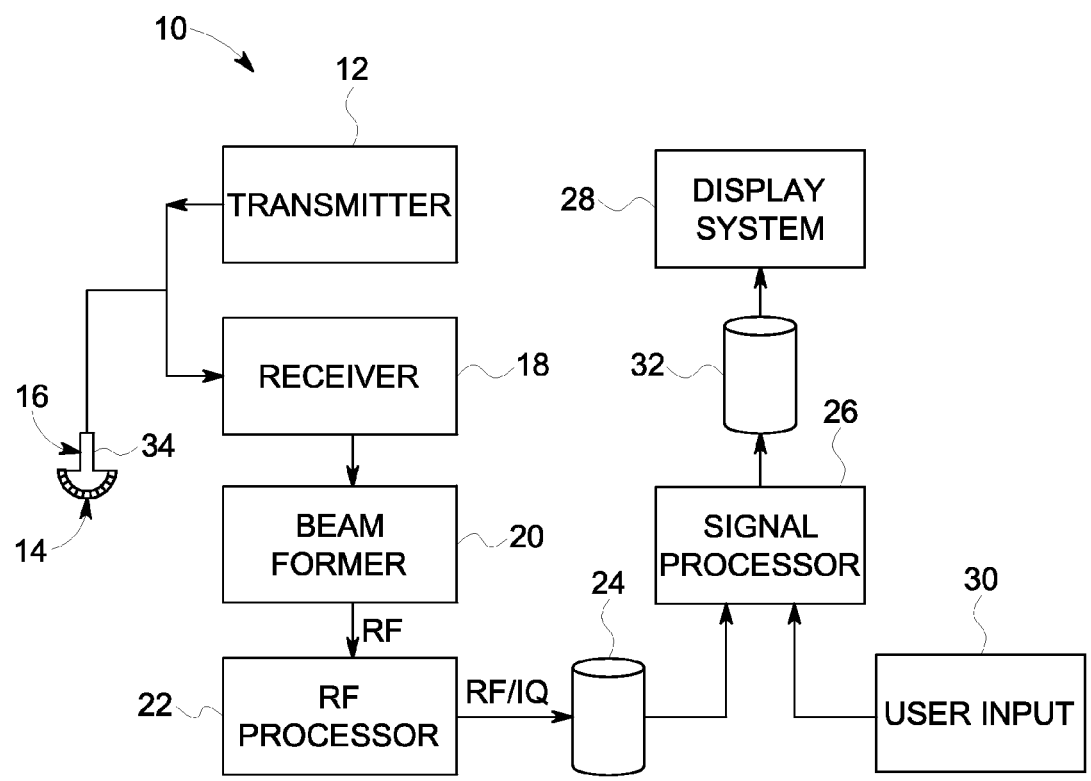
FIG. 1 is a block diagram of an ultrasound system formed in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and/or the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide ultrasound transducers and a method for manufacturing ultrasound transducers. An ultrasound transducer in accordance with various embodiments includes an array of acoustic elements, an integrated circuit, and an interposer. The interposer includes conductive elements that electrically connect the array of acoustic elements to the integrated circuit. An electrically conductive adhesive is engaged with the conductive elements of the interposer to electrically connect the interposer to the integrated circuit and/or the array of acoustic elements. The electrically conductive adhesive in various embodiments is anisotropically conductive.

A technical effect of at least some embodiments is providing a connection between various components of an ultrasound transducer using an electrically conductive adhesive, wherein the connection has a predetermined mechanical strength that facilitates preventing the connection from being severed, for example during operation and/or transport of the ultrasound transducer. A technical effect of at least some embodiments is providing a connection between various components of an ultrasound transducer using an electrically conductive adhesive, wherein adjacent electrical contacts or conductive elements of one or more of the components are not electrically shorted by the electrically conductive adhesive. A technical effect of at least some embodiments is providing an ultrasound transducer that can be manufactured in less time and/or that is more robust to temperature changes.

FIG. 1 is a block diagram of an ultrasound system 10 formed in accordance with various embodiments. The ultrasound system 10 may be used, for example, to acquire and process ultrasound images. The ultrasound system 10 includes a transmitter 12 that drives an array of acoustic elements 14 (i.e., transducer elements) within or formed as part of an ultrasound transducer 16 to emit pulsed ultrasonic signals into a body or other volume. The acoustic elements 14 may be arranged, for example, in one or two dimensions. A variety of geometries may be used. Each acoustic element 14 may be any type of acoustic element, such as, but not limited to, a piezoelectric ceramic (e.g., lead zirconate titanate (PZT)), a piezocomposite, piezoelectric crystals, a piezoelectric single crystal, a piezopolymer, and/or the like. The ultrasonic signals are back-scattered from density interfaces and/or structures in the body or other volume (e.g., blood cells, fatty tissue, and/or muscular tissue in a body) to produce echoes that return to the acoustic elements 14. The echoes are received by a receiver 18. The received echoes are passed through beamforming electronics 20, which performs beamforming and outputs an RF signal. The RF signal then passes through an RF processor 22. The RF processor 22 may include a complex demodulator (not shown) that demodulates the RF signal to form IQ data pairs representative of the echo signals. The RF or IQ signal data may then be routed directly to a memory 24 for storage (e.g., temporary storage).

The ultrasound system 10 also includes a signal processor 26 to process the acquired ultrasound information (e.g., RF signal data or IQ data pairs) and prepare frames of ultrasound information for display on a display system 28. The signal processor 26 is adapted to perform one or more processing operations according to a plurality of selectable ultrasound modalities on the acquired ultrasound information. Acquired ultrasound information may be processed and/or displayed in real-time during a scanning session as the echo signals are received. Additionally or alternatively, the ultrasound information may be stored temporarily in the memory 24 during a scanning session and then processed and/or displayed in less than real-time in a live or off-line operation.

The signal processor 26 is connected to a user input device 30 that may control operation of the ultrasound system 10. The user input device 30 may be any suitable device and/or user interface for receiving user inputs to control, for example, the type of scan or type of transducer to be used in a scan. The display system 28 includes one or more monitors that present patient information, including diagnostic ultrasound images to the user for diagnosis and/or analysis. The ultrasound system 10 may include a memory 32 for storing processed frames of acquired ultrasound information that are not scheduled to be displayed immediately. One or both of the memory 24 and the memory 32 may store three-dimensional (3D) data sets of the ultrasound data, where such 3D datasets are accessed to present 2D and/or 3D images. Multiple consecutive 3D datasets may also be acquired and stored over time, such as to provide real-time 3D or 4D display. The images may be modified and/or the display settings of the display system 28 may be manually adjusted using the user input device 30.

In addition to the acoustic elements 14, various other components of the ultrasound system 10 may be considered to be a component of the ultrasound transducer 16. For example, the transmitter 12, the receiver 18, and/or the beamforming electronics 20 may each be a component of the ultrasound transducer 16. In some embodiments, two or more components of the ultrasound system 10 are integrated into an integrated circuit (e.g., the integrated circuit 36 shown in FIGS. 2 and 3), which may be a component of the ultrasound transducer 16. For example, the transmitter 12, the receiver 18, and/or the beamforming electronics 20 may be integrated into an integrated circuit.

The ultrasound system 10 may include an ultrasound probe 34 that holds one or more various components of the ultrasound transducer 16. For example, as shown in FIG. 1, the ultrasound probe 34 holds the array of acoustic elements 14. In addition to the acoustic elements 14, and for example, the ultrasound probe 34 may hold the transmitter 12, the receiver 18, the beamforming electronics 20, and/or one or more integrated circuits that include any of the components 12, 18, and/or 20.

Figure 2:
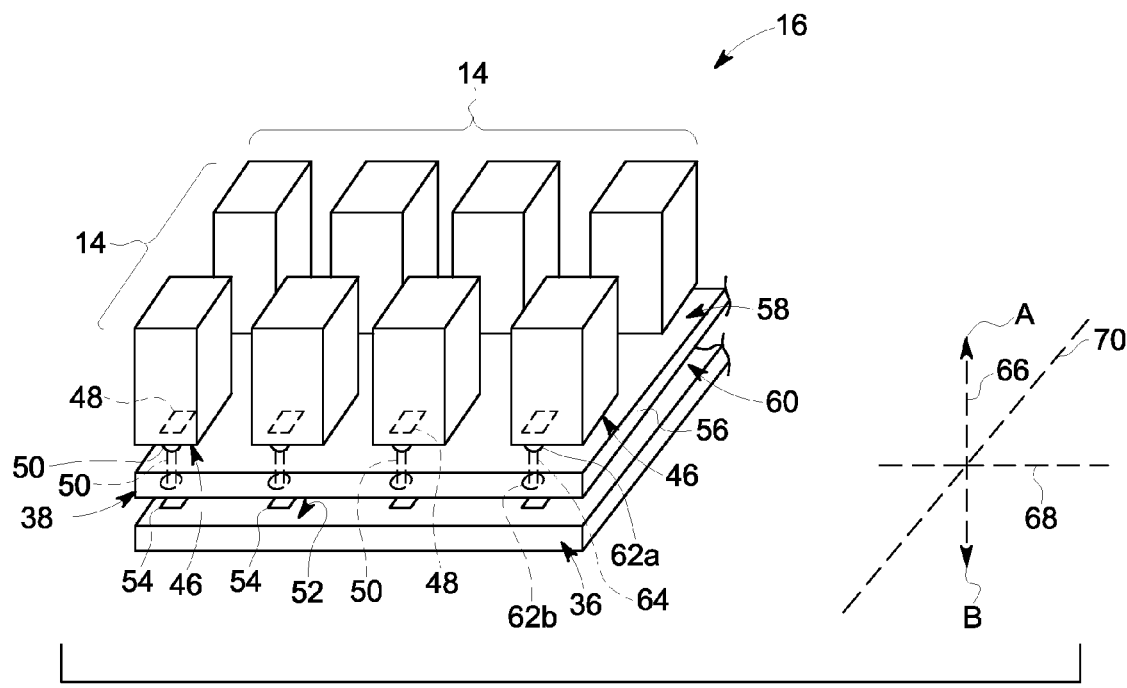
FIG. 2 is an exploded perspective view of an ultrasound transducer formed in accordance with various embodiments.
Figure 3:
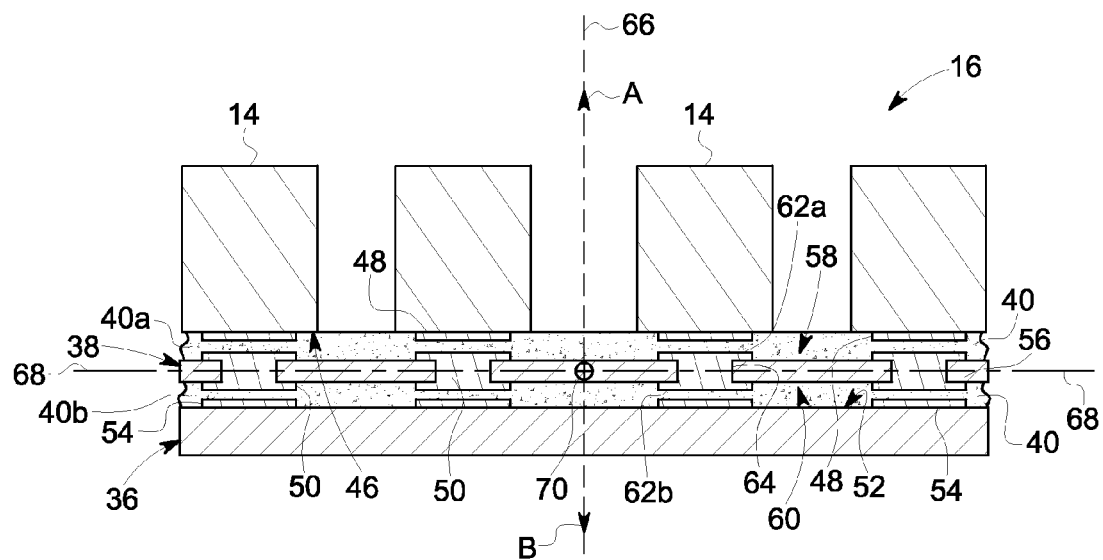
FIG. 3 is a cross-sectional view of the ultrasound transducer shown in FIG. 2.

FIG. 2 is an exploded perspective view of a portion of the ultrasound transducer 16 formed in accordance with various embodiments. FIG. 3 is an unexploded cross-sectional view of the ultrasound transducer 16. The ultrasound transducer 16 includes the array of acoustic elements 14, an integrated circuit 36, and an interposer 38 that electrically connects the acoustic elements 14 to the integrated circuit 36. As will be described in more detail below, the interposer 38 is electrically connected to the acoustic elements 14 and/or to the integrated circuit 36 using an electrically conductive adhesive 40 that is anisotropically conductive. The electrical conductive adhesive 40 also mechanically connects the interposer 38 to the acoustic elements 14 and/or to the integrated circuit 36. The electrically conductive adhesive 40 is not shown in FIG. 2 for clarity.

In an exemplary embodiment, the array of acoustic elements 14, the interposer 38, and the integrated circuit 36 are arranged in a stack, as can be seen in FIGS. 2 and 3. Within the stack, the interposer 38 extends between the integrated circuit 36 and the acoustic elements 14. Other relative arrangements of the acoustic elements 14, the interposer 38, and/or the integrated circuit 36 may be provided in addition or alternative to the stack.

Each acoustic element 14 includes an acoustic layer (not shown) that may be configured to generate and transmit acoustic energy into the body or other volume and receive backscattered acoustic signals from the body or other volume to create and display an image. The acoustic layer may include electrodes (not shown). The acoustic layer may be formed from any material(s), such as, but not limited to, a piezoelectric ceramic (e.g., lead zirconate titanate (PZT)), a piezocomposite, piezoelectric crystals, a piezoelectric single crystal, a piezopolymer, and/or the like. In some embodiments, the acoustic layer may include more than one sub-layer of one material or of two or more different materials. In other words, in some embodiments, the acoustic layer may include multiple sub-layers of the same material, while in other embodiments the acoustic layer may include multiple layers of different materials.

Each acoustic element may include one or more other layers in addition to the acoustic layer. For example, each acoustic element 14 may include one or more matching layers (not shown), one or more conductive film layers (not shown), and/or one or more dematching layers (not shown). Each acoustic element 14 may include any number of layers overall.

In an exemplary embodiment, each acoustic element 14 includes an interposer side 46 and an electrical contact 48 that extends along the interposer side 46. The electrical contacts 48 of the array of acoustic elements 14 are configured to be electrically connected to corresponding conductive elements 50 of the interposer 38 to establish an electrical connection between the acoustic elements 14 and the interposer 38, as will be described below. The electrical contacts 48 may each be any type of electrical contact having any structure. For example, the electrical contacts 48 are illustrated in FIGS. 2 and 3 as contact pads, but each electrical contact 48 may additionally or alternatively include any other structure, such as, but not limited to, solder balls, solder pads, stud bumps, plated bumps, and/or the like. In addition or alternatively to the electrical contacts 48, an exposed layer of an acoustic element 14 may be configured to provide the electrical connection of the acoustic element 14 to the corresponding conductive element 50.

The integrated circuit 36 may be any type of integrated circuit, such as, but not limited to, an application specific integrated circuit (ASIC) and/or the like. Various components of the ultrasound system 10 (shown in FIG. 1) may be included within the integrated circuit 36. In an exemplary embodiment, the integrated circuit 36 includes the transmitter 12 (shown in FIG. 1), the receiver 18 (shown in FIG. 1), and the beamforming electronics 20 (shown in FIG. 1) of the ultrasound system 10.

The integrated circuit 36 includes an interposer side 52 and a plurality of electrical contacts 54 that extend along the interposer side 52. The integrated circuit 36 may include electrical traces, electrical vias, and/or other electrical circuitry that facilitates performing the operations and functions of the various components of the integrated circuit 36. The electrical contacts 54 of the integrated circuit 36 are configured to be electrically connected to corresponding conductive elements 50 of the interposer 38 to establish an electrical connection between the integrated circuit 36 and the interposer 38, as will be described below. The electrical contacts 54 are illustrated in FIGS. 2 and 3 as contact pads. But, each electrical contact 54 may additionally or alternatively include any other structure, such as, but not limited to, solder balls, solder pads, stud bumps, plated bumps, and/or the like. The electrical contacts 54 of the integrated circuit 36 may include a plurality of different types of connections, such as, but not limited to, sensor pads, signal input/output (I/O), power, control functions, relatively high voltage connections, relatively low noise connections, and/or the like. For example, the electrical contacts 54 shown herein are sensor pads that are electrically connected to corresponding acoustic elements 14 through the interposer 38. The electrical contacts 54 of the integrated circuit 36 may further include electrical contacts (not shown) that represent other functions besides the sensor pads (such as, but not limited to, signal input/output (I/O), power, control functions, and/or the like) and that are electrically connected to the interposer 38 using the electrically conductive adhesive 40 in a substantially similar manner to that described below and illustrated herein with respect to the sensor pads.

The interposer 38 includes a substrate 56 and the conductive elements 50. The substrate 56 includes opposite sides 58 and 60. The side 58 faces the interposer sides 46 of the acoustic elements 14, while the side 60 faces the interposer side 52 of the integrated circuit 36. The conductive elements 50 are held by the substrate 56 and include electrical contacts 62a and 62b. The electrical contacts 62a of the conductive elements 50 extend along the side 58 of the substrate 56 for electrical connection to the electrical contacts 48 of the array of acoustic elements 14. The electrical contacts 62b of the conductive elements 50 extend along the side 60 of the substrate 56 for electrical connection to the electrical contacts 54 of the integrated circuit 36. In an exemplary embodiment, the electrical contacts 62a have the same pattern and pitch as the pattern and pitch of the electrical contacts 62b. Alternatively, the electrical contacts 62a and 62b have different patterns and pitches, for example in embodiments wherein the electrical contacts 48 of the array of acoustic elements 14 has a different pattern and/or pitch than the electrical contacts 54 of the integrated circuit 36.

In an exemplary embodiment, the conductive elements 50 are one-piece elements that include the electrical contacts 62a and 62b and an interior segment 64 that extends through the substrate 56 from the corresponding electrical contact 62a to the corresponding electrical contact 62b. In addition or alternatively, one or more of the conductive elements 50 includes an electrical via (not shown) that extends into the substrate 56, an electrical trace (not shown) that extends on the side 58, on the side 60, and/or on an internal layer (not shown) of the substrate 56, and/or other electrical circuitry. For example, in some embodiments, the electrical contacts 62a and 62b of a conductive element 50 are discrete structures that are mechanically and electrically connected together through one or more electrical traces of the interposer 38. Moreover, and for example, in some embodiments a conductive element 50 includes an electrically conductive via and the corresponding electrical contacts 62a and 62b of the conductive element 50 are contact pads of the electrically conductive via. The electrical contacts 62a and 62b may each be any type of electrical contact having any structure, such as, but not limited to, contact pads (as is illustrated herein), solder balls, solder pads, stud bumps, plated bumps, and/or the like. The conductive elements 50 may each be fabricated from any material(s), such as, but not limited to, a metal, an electrically conductive epoxy, silver epoxy, and/or the like. Although the electrical contacts 62a and 62b are each shown as extending outwardly on the respective sides 58 and 60, each electrical contact 62a and 62b may alternatively be flush with, or recessed relative to, the respective side 58 and 60.

The substrate 56 of the interposer 38 may be fabricated from any material(s). Examples of materials of the substrate 56 include, but are not limited to, a relatively low acoustic impedance material (e.g., an acoustic impedance of less than approximately 10 MRayls), an organic material, a polyimide (e.g., Kapton®), and/or the like. The substrate 56 is shown as including only a single layer, but the substrate 56 may include any number of layers. In some embodiments, the substrate 56 is generally flexible such that the interposer 38 is a flexible circuit (sometimes referred to as a "flex circuit").

In some embodiments, the interposer 38 is a cable that electrically connects the ultrasound transducer 16 to other components of the ultrasound system 10. For example, the interposer 38 may be a cable that provides signal, ground, control, and/or power connections between the ultrasound transducer 16 and the RF processor 22, the memory 24, the signal processor 26, the user input 30, the memory 32, and/or the display system. In some embodiments wherein the interposer 38 is a cable and a flexible circuit, the interposer 38 is a flat flexible cable, which is sometimes referred to as a "flat flex circuit", a "flat flexible conductor cable", a "flex cable", a "cable flex circuit", and/or a "flexible flat cable".

Referring now solely to FIG. 3, in an exemplary embodiment, the interposer 38 is electrically connected to both the array of acoustic elements 14 and the integrated circuit 36 using the electrically conductive adhesive 40. More specifically, a layer 40a of the electrically conductive adhesive 40 is engaged with both the conductive elements 50 of the interposer 38 and the electrical contacts 48 of the array of acoustic elements 14. Accordingly, the interposer 38 and the array of acoustic elements 14 are electrically connected together through the layer 40a of the electrically conductive adhesive 40. Similarly, a layer 40b of the electrically conductive adhesive 40 is engaged with both the conductive elements 50 of the interposer 38 and the electrical contacts 54 of the integrated circuit 36. Accordingly, the interposer 38 and the integrated circuit 36 are electrically connected together through the layer 40b of the electrically conductive adhesive 40. The interposer 38 thus electrically connects the array of acoustic elements 14 to the integrated circuit 36. Because the electrical contacts 54 of the integrated circuit 36 may include a plurality of different types of connections (e.g., relatively high voltage connections and relatively low noise connections), the electrically conductive adhesive layer 40b may be used to electrically connect a plurality of different types of connections of the integrated circuit 36 to the interposer 38. The layer 40b of the electrically conductive adhesive 40 may be referred to herein as a "first electrically conductive adhesive layer", while the layer 40a may be referred to herein as a "second electrically conductive adhesive layer".

As briefly described above, the electrically conductive adhesive 40 is anisotropically conductive. By "anisotropically conductive", it is meant that the electrically conductive adhesive 40 conducts electrical energy along at least a first axis, but does not conduct electrical energy along at least one other axis that is oriented at a non-zero angle relative to the first axis. The electrically conductive adhesive 40 is configured as anisotropically conductive such that the electrically conductive adhesive 40 conducts electrical energy along a conduction axis 66. As shown in FIG. 3, the conduction axis 66 extends through the height of the stack of the integrated circuit 36, the interposer 38, and the array of acoustic elements 14. The conduction axis 66 extends approximately perpendicular to the sides 58 and 60 of the substrate 56 of the interposer 38. The electrically conductive adhesive 40 is configured as anisotropically conductive such that the electrically conductive adhesive 40 does not conduct electrical energy along non-conduction axes 68 and 70. The non-conduction axes 68 and 70 extend approximately perpendicular to each other and to the conduction axis 66. The non-conduction axes 68 and 70 extend approximately parallel to the sides 58 and 60 of the substrate 56 of the interposer 38. The axes 66, 68, and 70 are also shown in FIG. 2 for clarity.

By conducting electrical energy along the conduction axis 66, the electrically conductive adhesive 40 electrically connects each of the conductive elements 50 of the interposer 38 to the corresponding electrical contact 48 of the array of acoustic elements 14 and to the corresponding electrical contact 54 of the integrated circuit 36. Specifically, the layer 40a of the electrically conductive adhesive 40 provides an electrical path, along the conduction axis 66, between each electrical contact 48 of the array of acoustic elements 14 and the electrical contact 62a of the corresponding conductive element 50. Similarly, the layer 40b of the electrically conductive adhesive 40 provides an electrical path, along the conduction axis 66, between each electrical contact 54 of the integrated circuit 36 and the electrical contact 62a of the corresponding conductive element 50. The layers 40a and 40b of the electrically conductive adhesive 40 conduct electrical energy along the conduction axis 66 in both of the directions A and B. Accordingly, the electrically conductive adhesive 40 is configured to conduct both the transmission and reception of ultrasound signals.

With respect to the axes 66, 68, and 70, the electrically conductive adhesive 40 only conducts electrical energy along the conduction axis 66. Because the layer 40a of the electrically conductive adhesive 40 does not conduct electrical energy along the non-conduction axes 68 and 70, the layer 40a does not conduct electrical energy between adjacent electrical contacts 48 of the array of acoustic elements 14. Moreover, the layer 40a does not conduct electrically energy between adjacent electrical contacts 62a of the interposer 38. Accordingly, the anisotropic conductivity of the electrically conductive adhesive 40 prevents adjacent electrical contacts 48 of the array of acoustic elements 14 from electrically shorting and prevents adjacent electrical contacts 62a of the interposer 38 from electrically shorting. Moreover, the layer 40b of the electrically conductive adhesive 40 does not conduct electrical energy between adjacent electrical contacts 54 of the integrated circuit 36 because the layer 40b does not conduct electrical energy along the non-conduction axes 68 and 70. The layer 40b also does not conduct electrical energy between adjacent electrical contacts 62b of the interposer 38. The anisotropic conductivity of the electrically conductive adhesive 40 thus prevents adjacent electrical contacts 54 of the integrated circuit 36 from electrically shorting and prevents adjacent electrical contacts 62b of the interposer 38 from electrically shorting.

In an exemplary embodiment, the layer 40a of the electrically conductive adhesive 40 extends over and engages both the side 58 of the substrate 56 of the interposer 38 and the interposer sides 46 of the acoustic elements 14. The layer 40a thus provides a mechanical connection between the interposer 38 and the array of acoustic elements 14 (in addition to the mechanical connection between the electrical contacts 48 and the electrical contacts 62a provided by the layer 40a). In some embodiments, the layer 40a of the electrically conductive adhesive 40 does not extend over and engage the side 58 of the substrate 56 and the interposer sides 46 of the acoustic elements 14. For example, the layer 40a of the electrically conductive adhesive 40 may only engage the electrical contacts 48 and 62a. In some embodiments, a non-electrically conductive adhesive (not shown; e.g., silver epoxy) extends over and engages both the side 58 of the substrate 56 and the interposer sides 46 of the acoustic elements 14 to provide a mechanical connection between the substrate 56 and the acoustic elements 14 (in addition to the mechanical connection between the electrical contacts 48 and the electrical contacts 62a provided by the layer 40a). In addition or alternative to the electrically conductive adhesive 40 and/or the non-electrically conductive adhesive, in some embodiments any other structure, fastener, means, and/or the like may be used to mechanically connect the interposer 38 and the array of acoustic elements 14.

The layer 40b of the electrically conductive adhesive 40 extends over and engages both the side 60 of the substrate 56 of the interposer 38 and the interposer side 52 of the integrated circuit 36. The layer 40b provides a mechanical connection between the interposer 38 and the integrated circuit 36, which is in addition to the mechanical connection between the electrical contacts 54 and the electrical contacts 62a provided by the layer 40b. In some embodiments, the layer 40b of the electrically conductive adhesive 40 does not extend over and engage the side 60 of the interposer 38 and the interposer side 52 of the integrated circuit 36 (e.g., the layer 40b may only engage the electrical contacts 54 and 62b). In some embodiments, a non-electrically conductive adhesive (not shown; e.g., silver epoxy) extends over and engages both the side 60 of the interposer 38 and the interposer side 52 of the integrated circuit 36 to provide a mechanical connection between the substrate 56 and the integrated circuit 36 (in addition to the mechanical connection between the electrical contacts 54 and the electrical contacts 62b provided by the layer 40b). In addition or alternative to the electrically conductive adhesive 40 and/or the non-electrically conductive adhesive, in some embodiments any other structure, fastener, means, and/or the like may be used to mechanically connect the interposer 38 and the integrated circuit 36.

Each layer 40a and 40b of the electrically conductive adhesive 40 may be fabricated from any material(s) and may be any type of adhesive that enables the electrically conductive adhesive 40 to function as described and/or illustrated herein. In some embodiments, the layer 40a and/or the layer 40b includes electrically conductive particles (e.g., polymer spheres, metallic spheres, metallized polymer spheres, and/or the like) suspended in an adhesive. Examples of types of adhesives include films, pastes, gels, and/or the like. Various parameters of the electrically conductive adhesive 40 may be selected to enable the electrically conductive adhesive 40 to provide electrical conductivity over a range of environmental conditions (e.g., temperature, humidity, and/or the like). Such various parameters of the electrically conductive adhesive may include, but are not limited to, a filling degree and/or a size (e.g., a diameter) of any electrically conductive particles of the electrically conductive adhesive. The layers 40a and 40b may be different types of adhesives from each other and/or may include one or more different materials than each other. In some embodiments, the layers 40a and 40b are the same type of adhesive and/or include the same materials. Moreover, in some embodiments, the layer 40a and/or the layer 40b is a combination of two or more different types of adhesive (e.g., a combination of an electrically conductive paste and an electrically conductive film).

In an exemplary embodiment, both the array of acoustic elements 14 and the integrated circuit 36 are electrically and mechanically connected to the interposer 38 using the electrically conductive adhesive 40. But, in some embodiments, only the integrated circuit or the array of acoustic elements 14 is electrically and mechanically connected to the interposer 38 using the electrically conductive adhesive 40. In other words, in some embodiments, the ultrasound transducer 16 does not include the layer 40a or does not include the layer 40b of the electrically conductive adhesive 40.

In some alternative embodiments, the ultrasound transducer 16 does not include the interposer 38. In such embodiments wherein the ultrasound transducer 16 does not include the interposer 38, the array of acoustic elements 14 and the integrated circuit 36 may be directly electrically and mechanically connected together using an electrically conductive adhesive that is anisotropically conductive in a manner substantially similar to that described and illustrated herein with respect to the electrically conductive adhesive 40. Specifically, the electrical contacts 48 of the array of acoustic elements 14 and the electrical contacts 54 of the integrated circuit 36 may be directly electrically and mechanically connected together using an electrically conductive adhesive that is anisotropically conductive.

Figure 4:
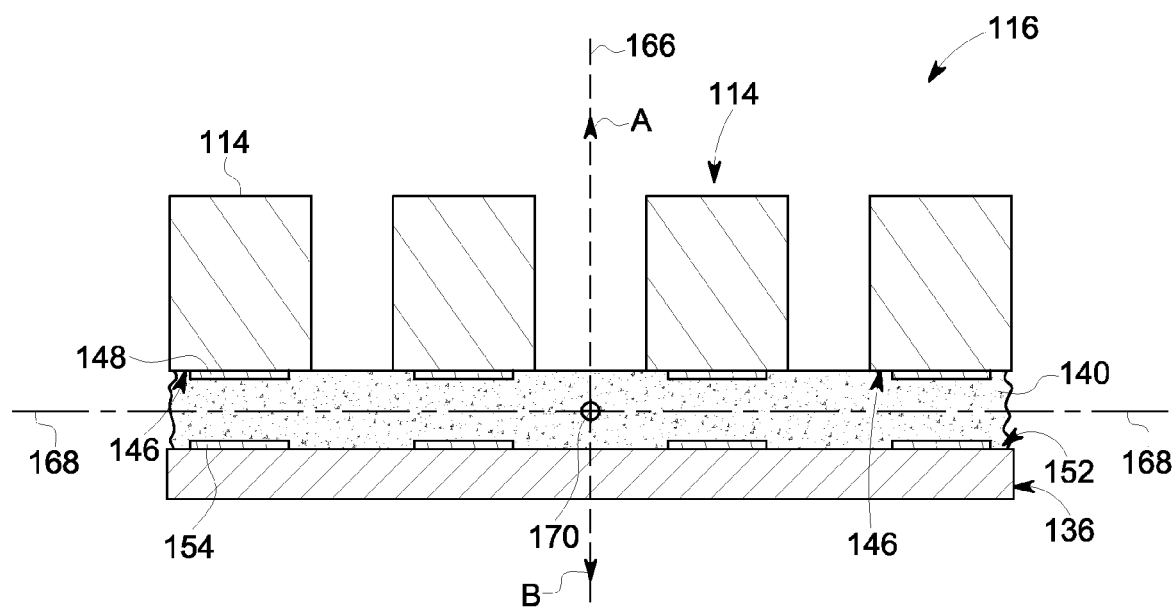
FIG. 4 is a cross-sectional view of another ultrasound transducer formed in accordance with various embodiments.

FIG. 4 is a cross-sectional view of another ultrasound transducer 116 formed in accordance with various embodiments. FIG. 4 illustrates an embodiment wherein the ultrasound transducer 116 does not include an interposer (e.g., the interposer 38). The ultrasound transducer 116 includes an array of acoustic elements 114 and an integrated circuit 136. The acoustic elements 114 and the integrated circuit 136 are electrically connected together using an electrically conductive adhesive 140 that is anisotropically conductive. The electrical conductive adhesive 140 also mechanically connects the acoustic elements 114 to the integrated circuit 136.

In an exemplary embodiment, each of the acoustic elements 114 includes an integrated circuit side 146 and an electrical contact 148 that extends along the integrated circuit side 146. The electrical contacts 148 of the array of acoustic elements 114 are configured to be electrically connected to electrical contacts 154 of the integrated circuit 136 to establish an electrical connection between the acoustic elements 14 and the integrated circuit 136. The electrical contacts 148 may each be any type of electrical contact having any structure. For example, the electrical contacts 148 are illustrated in FIG. 4 as contact pads, but each electrical contact 148 may additionally or alternatively include any other structure, such as, but not limited to, solder balls, solder pads, stud bumps, plated bumps, and/or the like. In addition or alternatively to the electrical contacts 148, an exposed layer of an acoustic element 114 may be configured to provide the electrical connection of the acoustic element 114 to the corresponding electrical contact 154.

The integrated circuit 136 may be any type of integrated circuit, such as, but not limited to, an application specific integrated circuit (ASIC) and/or the like. Various components of the ultrasound system 10 (shown in FIG. 1) may be included within the integrated circuit 136. In an exemplary embodiment, the integrated circuit 136 includes the transmitter 12 (shown in FIG. 1), the receiver 18 (shown in FIG. 1), and the beamforming electronics 20 (shown in FIG. 1) of the ultrasound system 10.

The integrated circuit 136 includes an array side 152 and a plurality of the electrical contacts 154 that extend along the array side 152. The integrated circuit 136 may include electrical traces, electrical vias, and/or other electrical circuitry that facilitates performing the operations and functions of the various components of the integrated circuit 136. The electrical contacts 154 of the integrated circuit 136 are configured to be electrically connected to corresponding electrical contacts 148 of the acoustic elements 114 to establish an electrical connection between the integrated circuit 136 and the acoustic elements 114. The electrical contacts 154 are illustrated in FIG. 4 as contact pads. But, each electrical contact 154 may additionally or alternatively include any other structure, such as, but not limited to, solder balls, solder pads, stud bumps, plated bumps, and/or the like.

As briefly described above, the electrically conductive adhesive 140 is used to electrically connect the array of acoustic elements 114 to the integrated circuit 136. More specifically, the electrically conductive adhesive 140 is engaged with both the electrical contacts 148 of the array of acoustic elements 114 and with the electrical contacts 154 of the integrated circuit 136. The electrically conductive adhesive 140 thus electrically connects the array of acoustic elements 114 to the integrated circuit 136.

The electrically conductive adhesive 140 is anisotropically conductive. The electrically conductive adhesive 140 is configured as anisotropically conductive such that the electrically conductive adhesive 140 conducts electrical energy along a conduction axis 166. The electrically conductive adhesive 140 is configured as anisotropically conductive such that the electrically conductive adhesive 140 does not conduct electrical energy along non-conduction axes 168 and 170. The non-conduction axes 168 and 170 extend approximately perpendicular to each other and to the conduction axis 166. By conducting electrical energy along the conduction axis 166, the electrically conductive adhesive 140 electrically connects the electrical contacts 154 of the integrated circuit 136 to the corresponding electrical contacts 148 of the array of acoustic elements 114. Specifically, the electrically conductive adhesive 140 provides an electrical path, along the conduction axis 166, between each electrical contact 148 of the array of acoustic elements 114 and each electrical contact 154 of the integrated circuit 136. The electrically conductive adhesive 140 conducts electrical energy along the conduction axis 166 in both of the directions A and B. Accordingly, the electrically conductive adhesive 140 is configured to conduct both the transmission and reception of ultrasound signals.

With respect to the axes 166, 168, and 170, the electrically conductive adhesive 140 only conducts electrical energy along the conduction axis 166. Because the electrically conductive adhesive 140 does not conduct electrical energy along the non-conduction axes 168 and 170, the electrically conducive adhesive 140 does not conduct electrical energy between adjacent electrical contacts 148 of the array of acoustic elements 114. Moreover, the electrically conductive adhesive 140 does not conduct electrically energy between adjacent electrical contacts 154 of the integrated circuit 136. Accordingly, the anisotropic conductivity of the electrically conductive adhesive 140 prevents adjacent electrical contacts 148 of the array of acoustic elements 114 from electrically shorting and prevents adjacent electrical contacts 154 of the integrated circuit 136 from electrically shorting.

In an exemplary embodiment, the electrically conductive adhesive 140 extends over and engages both the integrated circuit sides 146 of the acoustic elements 114 and the array side 152 of the integrated circuit 136. The electrically conductive adhesive 140 thus provides a mechanical connection between the integrated circuit 136 and the array of acoustic elements 114 (in addition to the mechanical connection between the electrical contacts 148 and the electrical contacts 154 provided by the electrically conductive adhesive 140). In some embodiments, the electrically conductive adhesive 140 does not extend over and engage the sides 146 and 152. For example, the electrically conductive adhesive 140 may only engage the electrical contacts 148 and 154. In some embodiments, a non-electrically conductive adhesive (not shown; e.g., silver epoxy) extends over and engages both the side 146 and the side 152 to provide a mechanical connection between the array of acoustic elements 114 and the integrated circuit 136 (in addition to the mechanical connection between the electrical contacts 148 and the electrical contacts 154 provided by the electrically conductive adhesive 140). In addition or alternative to the electrically conductive adhesive 140 and/or the non-electrically conductive adhesive, in some embodiments any other structure, fastener, means, and/or the like may be used to mechanically connect the integrated circuit 136 to the array of acoustic elements 114.

The electrically conductive adhesive 140 may be fabricated from any material(s) and may by any type of adhesive that enables the electrically conductive adhesive 140 to function as described and/or illustrated herein. In some embodiments, the electrically conductive adhesive 140 includes electrically conductive particles (e.g., polymer spheres, metallic spheres, metallized polymer spheres, and/or the like) suspended in an adhesive. Examples of types of adhesives include films, pastes, gels, and/or the like. In some embodiments, the electrically conductive adhesive 140 is a combination of two or more different types of adhesive (e.g., a combination of an electrically conductive paste and an electrically conductive film).

Figure 5:
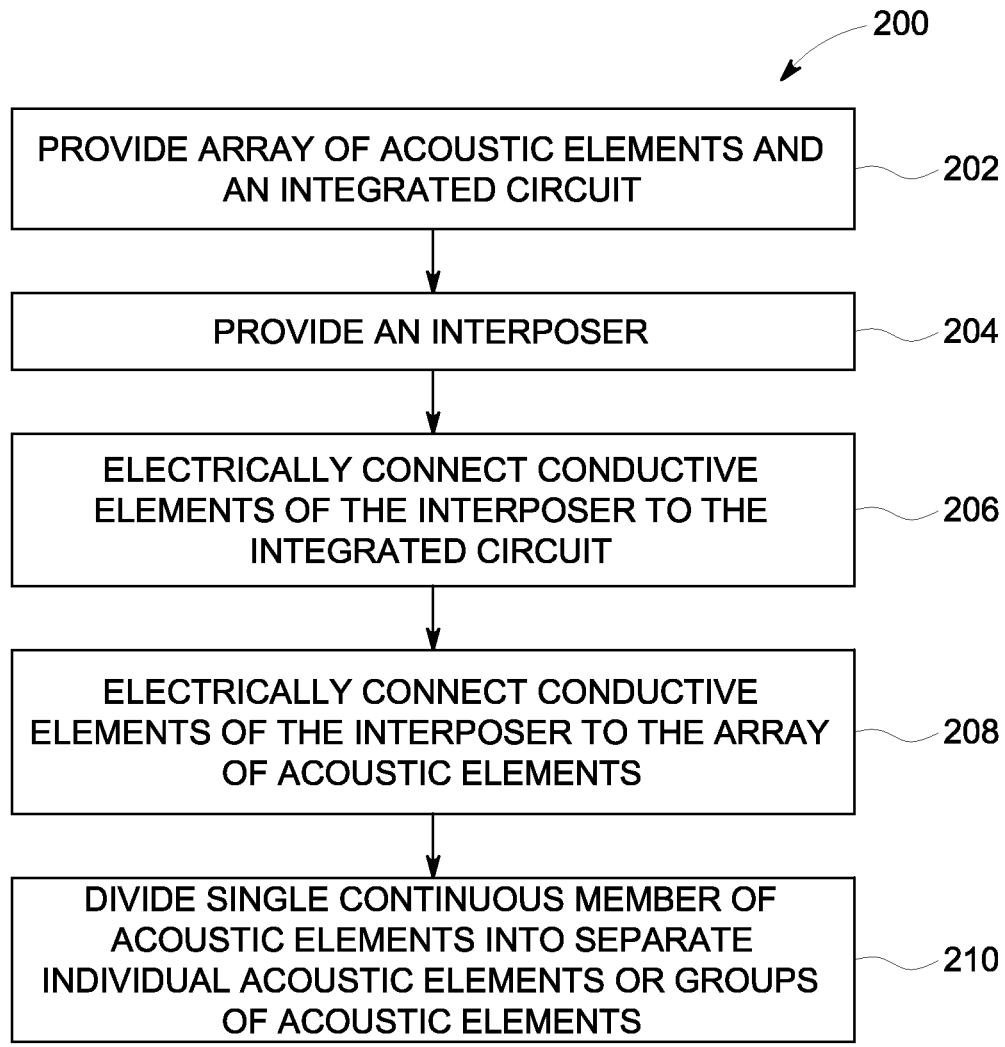
FIG. 5 is a flowchart illustrating a method for manufacturing an ultrasound transducer in accordance with various embodiments.

FIG. 5 is a flowchart illustrating a method 200 for manufacturing an ultrasound transducer in accordance with various embodiments. Exemplary uses of the method 200 include manufacturing the ultrasound transducer 16 shown in FIGS. 1-3 or the ultrasound transducer 116 shown in FIG. 4. The method 200 includes, at 202, providing an array of acoustic elements (e.g., the acoustic elements 14 shown in FIGS. 1-3 or the acoustic elements 114 shown in FIG. 4) and an integrated circuit (e.g., the integrated circuit 36 shown in FIGS. 1-3 or the integrated circuit 136 shown in FIG. 4). The array of acoustic elements may include electrical contacts (e.g., the electrical contacts 48 shown in FIGS. 2 and 3). In some embodiments, the array of acoustic elements are provided, at 202, as a single continuous member (e.g., a single continuous sheet). In other embodiments, the array of acoustic elements are provided, at 202, as a plurality of separate individual acoustic elements or as a plurality of separate groups of acoustic elements.

At 204, the method 200 includes providing an interposer (e.g., the interposer 38 shown in FIG. 1-3), wherein the interposer includes a plurality of conductive elements (e.g., the conductive elements 50 shown in FIGS. 2 and 3). The providing steps 202 and 204 may include arranging the array of acoustic elements, the integrated circuit, and the interposer in a stack, wherein the interposer extends between the integrated circuit and the array of acoustic elements within the stack. The interposer may include a side that faces the integrated circuit and a side that faces the array of acoustic elements, wherein the sides may be the same side or opposite sides. For example, when arranged with the integrated circuit and the array of acoustic elements within a stack, the interposer has a side that faces the array of acoustic elements and an opposite side that faces the integrated circuit. Moreover, and for example, when the interposer is not arranged with the integrated circuit and the array of acoustic elements within a stack, the same side of the interposer may face both the integrated circuit and the array of acoustic elements or different sides of the interposer may face the integrated circuit and the array of acoustic elements.

At 206, the method 200 includes electrically connecting the conductive elements of the interposer to the integrated circuit. Specifically, electrical contacts of the integrated circuit are electrically connected to the conductive elements of the interposer at 206. Electrically connecting the interposer to the integrated circuit at 206 may include applying to the interposer and/or the integrated circuit an electrically conductive adhesive (e.g., the electrically conductive adhesive 40 shown in FIG. 3) that is anisotropically conductive such that the electrically conductive adhesive is engaged between the conductive elements of the interposer and the electrical contacts of the integrated circuit. The anisotropic electrically conductive adhesive may be applied at 206 such that the anisotropic electrically conductive adhesive functions in a manner substantially similar to that described and illustrated herein with respect to the layer 40a (shown in FIGS. 2 and 3) of the anisotropic electrically conductive adhesive 40. For example, the anisotropic electrically conductive adhesive may only conduct electrical energy along an axis that extends approximately perpendicular to the side of the interposer that faces the integrated circuit.

As described above, the electrical contacts of the integrated circuit may include a plurality of different types of connections, such as, but not limited to, sensor pads, signal input/output (I/O), power, control functions, relatively high voltage connections, relatively low noise connections, and/or the like. In such embodiments, the step 206 of electrically connecting the conductive elements of the interposer to the integrated circuit includes electrically connecting a plurality of different types of connections of the integrated circuit to the interposer in a single operation (e.g., a single cure and pressure cycle), which may reduce a cost, time, difficulty, and/or complexity of manufacturing the ultrasound transducer. Moreover, electrically connecting the plurality of different types of connections of the integrated circuit to the interposer in a single operation may enable the electrical contacts of the integrated circuit to be more closely spaced, which may provide the integrated circuit and/or the interposer with a smaller footprint.

At 208, the method 200 includes electrically connecting the conductive elements of the interposer to the array of acoustic elements. In an exemplary embodiment, electrical contacts of the array of acoustic elements are electrically connected to the conductive elements of the interposer at 208. Electrically connecting the interposer to the array of acoustic elements 208 may include applying to the interposer and/or the array of acoustic elements an electrically conductive adhesive (e.g., the electrically conductive adhesive 40 shown in FIG. 3) that is anisotropically conductive such that the electrically conductive adhesive is engaged between the conductive elements of the interposer and the electrical contacts of the array of acoustic elements. The anisotropic electrically conductive adhesive may be applied at 208 such that the anisotropic electrically conductive adhesive functions in a manner substantially similar to that described and illustrated herein with respect to the layer 40b (shown in FIGS. 2 and 3) of the anisotropic electrically conductive adhesive 40. For example, the anisotropic electrically conductive adhesive may only conduct electrical energy along an axis that extends approximately perpendicular to the side of the interposer that faces the array of acoustic elements.

In embodiments wherein the acoustic elements are provided, at 202, as a single continuous member, the method 200 may include, at 210, dividing the single continuous member of the acoustic elements into a plurality of separate individual acoustic elements or into two or more separate groups of acoustic elements. In such embodiments, the step 208 of electrically connecting the conductive elements of the interposer to the array of acoustic elements is performed in a single operation (e.g., a single cure and pressure cycle), which may reduce a cost, time, difficulty, and/or complexity of manufacturing the ultrasound transducer. In embodiments wherein the acoustic elements are provided, at 202, as a plurality of separate individual acoustic elements or two or more separate groups of acoustic elements, each individual acoustic element or group of acoustic elements may be electrically connected to the interposer in a different operation of step 208.

Although the method steps 208 and 210 are shown herein, and described above, as being performed after the method step 206, alternatively the step 208 and/or the step 210 is performed before, or simultaneously with, the step 206.

Figure 6:
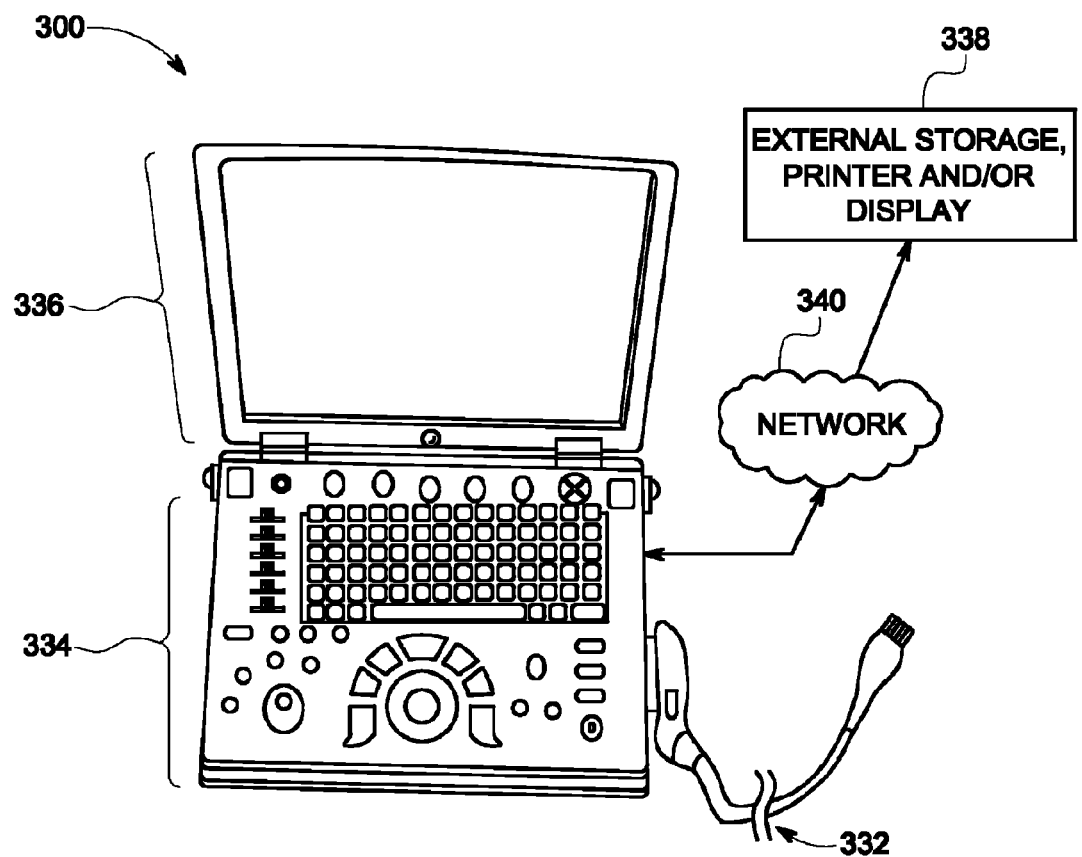
FIG. 6 is a diagram illustrating a three-dimensional (3D) capable miniaturized ultrasound system in which various embodiments may be implemented.
Figure 7:
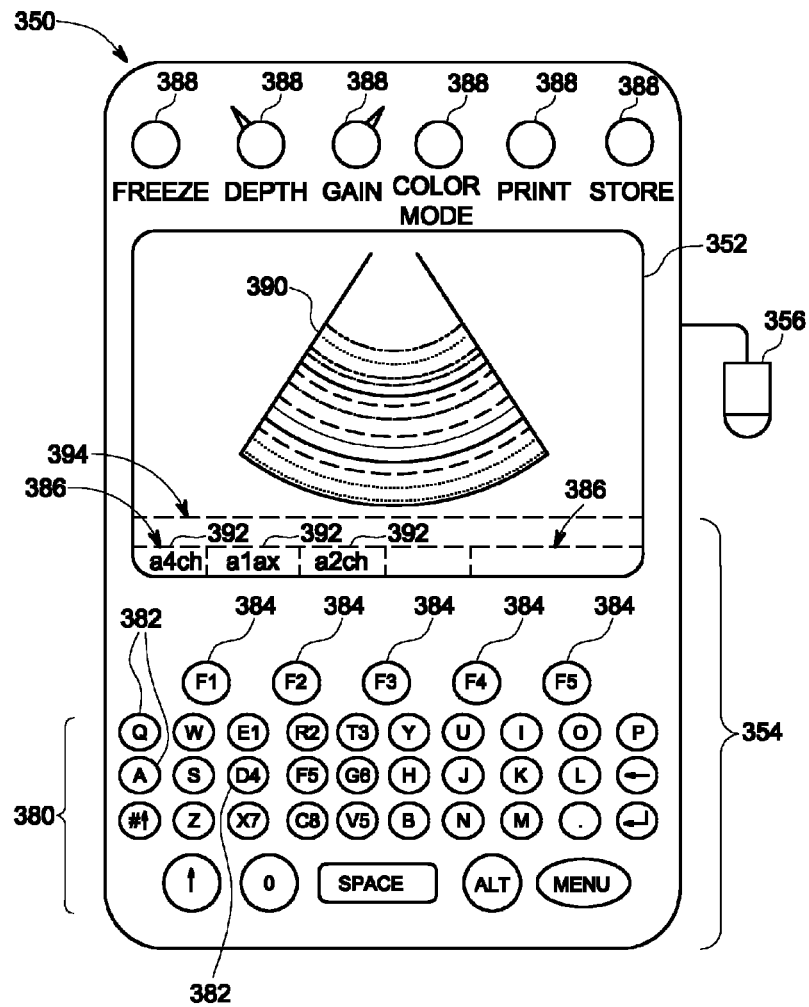
FIG. 7 is a diagram illustrating a 3D capable hand carried or pocket-sized ultrasound imaging system in which various embodiments may be implemented.
Figure 8:
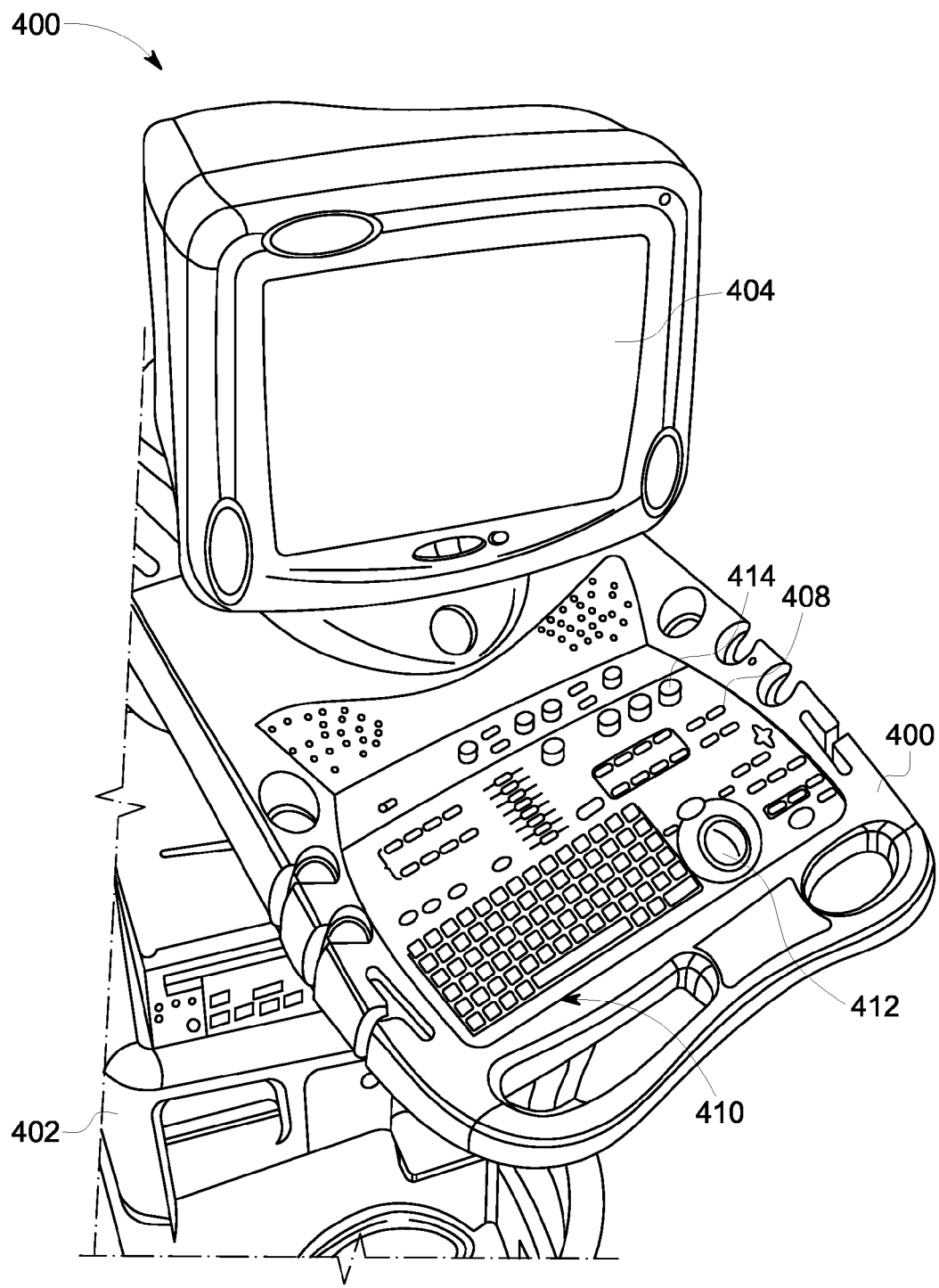
FIG. 8 is a diagram illustrating a 3D capable console type ultrasound imaging system in which various embodiments may be implemented.

Referring again to FIG. 1, the ultrasound system 10 may be embodied in a small-sized system, such as laptop computer or pocket sized system as well as in a larger console-type system. FIGS. 6 and 7 illustrate small-sized systems, while FIG. 8 illustrates a larger system.

FIG. 6 illustrates a 3D-capable miniaturized ultrasound system 300 having an ultrasound transducer 332 that may be configured to acquire 3D ultrasonic data or multi-plane ultrasonic data. For example, the ultrasound transducer 332 may have a 2D array of acoustic elements as discussed previously with respect to the ultrasound transducer 16 of FIG. 1. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

FIG. 7 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, and an ultrasound transducer 356. The display 352 may be, for example, a 320×320 pixel color LCD display (on which a medical image 390 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 300 may provide the same scanning and processing functionality as the system 10 (shown in FIG. 1)

FIG. 8 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and/or the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

Figure 9:
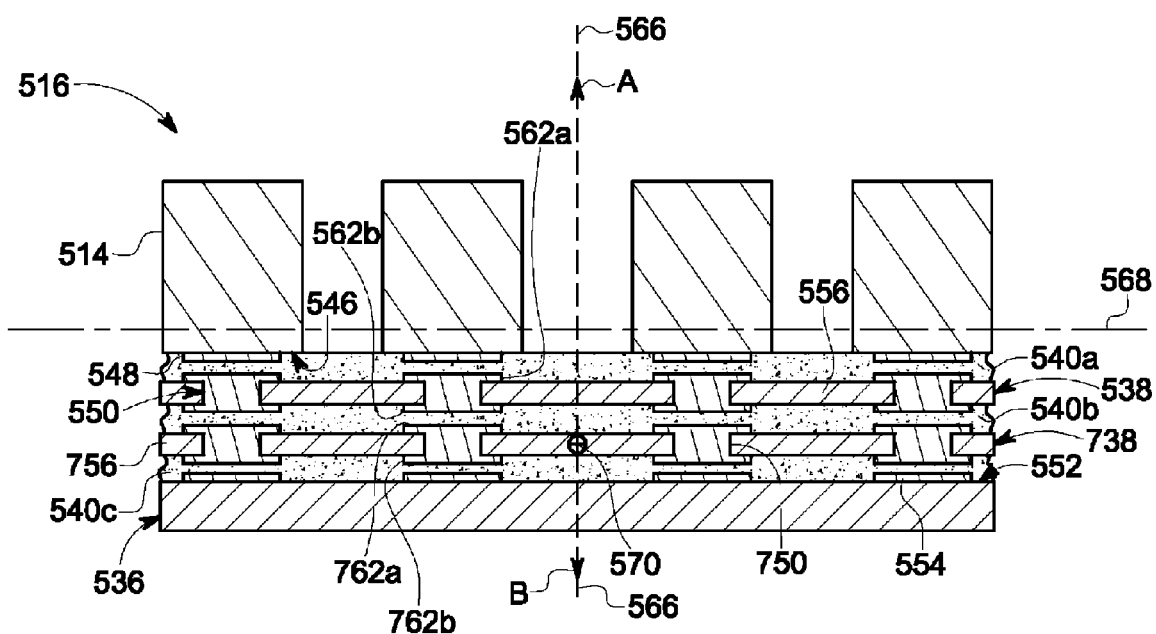
FIG. 9 is a cross-sectional view of another ultrasound transducer formed in accordance with various embodiments.

FIG. 9 is a cross-sectional view of another ultrasound transducer 516 formed in accordance with various embodiments. FIG. 9 illustrates an embodiment wherein the ultrasound transducer 516 includes two interposers 538 and 738. The ultrasound transducer 516 includes an array of acoustic elements 514, an integrated circuit 536, and the interposers 538 and 738, which electrically connect the acoustic elements 514 to the integrated circuit 536. The interposer 538 may be referred to herein as a "first interposer", while the interposer 738 may be referred to herein as a "second interposer".

In an exemplary embodiment, each acoustic element 514 includes an interposer side 546 and an electrical contact 548 that extends along the interposer side 546. The integrated circuit 536 includes an interposer side 552 and a plurality of electrical contacts 554 that extend along the interposer side 552.

The interposers 538 and 738 include respective substrates 556 and 756 and respective conductive elements 550 and 750. The conductive elements 550 are held by the substrate 556 of the interposer 538 and include electrical contacts 562a and 562b. Similarly, the conductive elements 750 of the interposer 738 are held by the substrate 756 and include electrical contacts 762a and 762b. The conductive elements 550 may be referred to herein as "first conductive elements", while the conductive elements 750 may be referred to as "second conductive elements".

The array of acoustic elements 514 is electrically connected to the integrated circuit 536 using an electrically conductive adhesive 540. More specifically, a layer 540a of the electrically conductive adhesive 540 is engaged with both the electrical contacts 562a of the interposer 538 and the electrical contacts 548 of the array of acoustic elements 514. Accordingly, the interposer 538 and the array of acoustic elements 514 are electrically connected together through the layer 540a of the electrically conductive adhesive 540. Another layer 540b of the electrically conductive adhesive 540 is engaged with both the electrical contacts 562b of the interposer 538 and the electrical contacts 762a of the interposer 738. The interposers 538 and 738 are thus electrically connected together through the layer 540b of the electrically conductive adhesive 540. A layer 540c of the electrically conductive adhesive 540 is engaged with both the electrical contacts 762b of the interposer 738 and the electrical contacts 554 of the integrated circuit 536. Accordingly, the interposer 738 and the integrated circuit 536 are electrically connected together through the layer 540c of the electrically conductive adhesive 540. The interposers 538 and 738 thus electrically connect the array of acoustic elements 514 to the integrated circuit 536. The layer 540a of the electrically conductive adhesive 540 may be referred to herein as a "first electrically conductive adhesive layer", while the layers 540b and 540c of the electrically conductive adhesive 540 may be referred to herein as a "second electrically conductive adhesive layer" and a "third electrically conductive adhesive layer", respectively.

The electrically conductive adhesive 540 is anisotropically conductive. The electrically conductive adhesive 540 is configured as anisotropically conductive such that the electrically conductive adhesive 540 conducts electrical energy along a conduction axis 566. The electrically conductive adhesive 540 is configured as anisotropically conductive such that the electrically conductive adhesive 540 does not conduct electrical energy along non-conduction axes 568 and 570. The non-conduction axes 568 and 570 extend approximately perpendicular to each other and to the conduction axis 566. By conducting electrical energy along the conduction axis 566, the electrically conductive adhesive 540 electrically connects the electrical contacts 554 of the integrated circuit 536 to the corresponding electrical contacts 548 of the array of acoustic elements 514. Specifically, the electrically conductive adhesive 540 provides an electrical path (in addition to the conductive elements 550 and 750 of the interposers 538 and 738, respectively), along the conduction axis 566, between each electrical contact 548 of the array of acoustic elements 514 and each electrical contact 554 of the integrated circuit 536. The electrically conductive adhesive 540 conducts electrical energy along the conduction axis 566 in both of the directions A and B. Accordingly, the electrically conductive adhesive 540 is configured to conduct both the transmission and reception of ultrasound signals.

With respect to the axes 566, 568, and 570, the electrically conductive adhesive 540 only conducts electrical energy along the conduction axis 566. Because the electrically conductive adhesive 540 does not conduct electrical energy along the non-conduction axes 568 and 570, the electrically conductive adhesive 540 does not conduct electrical energy between adjacent electrical contacts 548 of the array of acoustic elements 514. Moreover, the electrically conductive adhesive 540 does not conduct electrically energy between adjacent conductive elements 550 of the interposer 538, does not conduct electrical energy between adjacent conductive elements 750 of the interposer 738, and does not conduct electrical energy between adjacent electrical contacts 554 of the integrated circuit 536. Accordingly, the anisotropic conductivity of the electrically conductive adhesive 540 prevents adjacent electrical contacts 548 of the array of acoustic elements 514 from electrically shorting, prevents adjacent conductive elements 550 of the interposer 538 from electrically shorting, prevents adjacent conductive elements 750 of the interposer 738 from electrically shorting, and prevents adjacent electrical contacts 554 of the integrated circuit 536 from electrically shorting.

Figure 10:
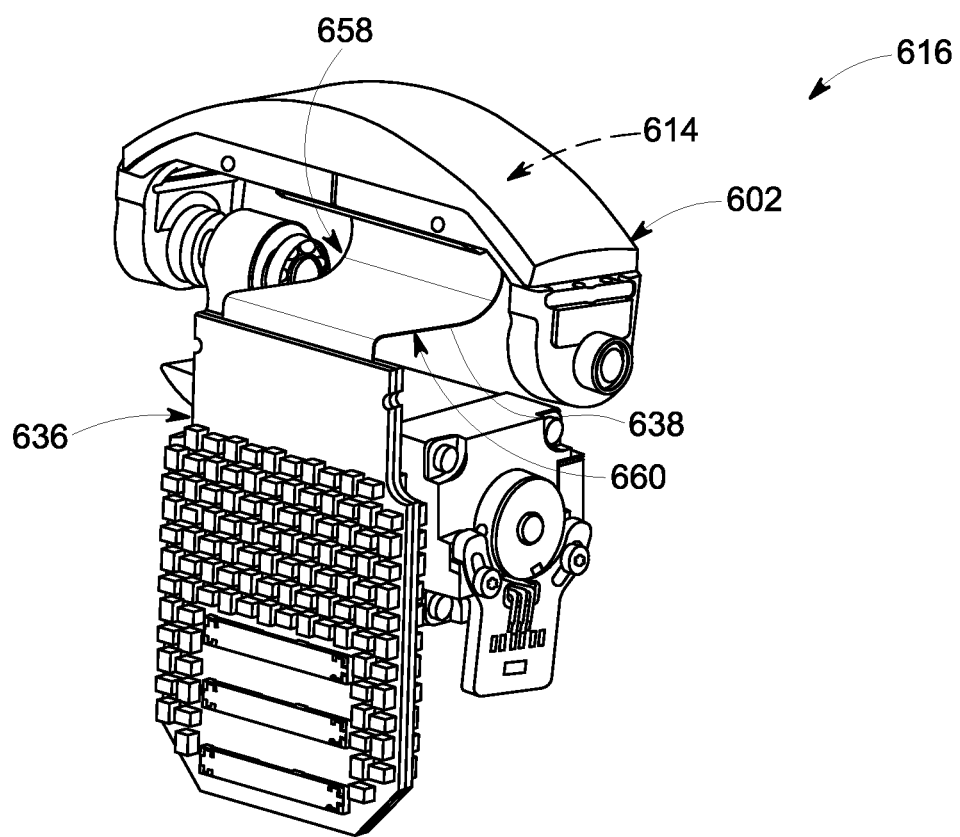
FIG. 10 is a perspective view of a portion of another ultrasound transducer formed in accordance with various embodiments.

FIG. 10 is a perspective view of a portion of another ultrasound transducer 616 formed in accordance with various embodiments. As described above, the ultrasound transducer embodiments described and/or illustrated herein are not limited to the stacked arrangement of the integrated circuit 36 (shown in FIGS. 1-3), the interposer 38 (shown in FIGS. 1-3), and the array of acoustic elements 14 (shown in FIGS. 1-3). FIG. 10 illustrates another embodiment of an ultrasound transducer 616 having an integrated circuit 636, an interposer 638, and an array of acoustic elements 614 that are not arranged in a stack.

The ultrasound transducer 616 includes a scan head 602 and one or more integrated circuits 636. The scan head 602 includes the array of acoustic elements 614. The integrated circuit 636 is located remote from the scan head 602 such that the integrated circuit 636 is not arranged within a stack with the array of acoustic elements 614. The integrated circuit 636 is electrically connected to the array of acoustic elements 614 via the interposer 638. The interposer 638 is a flex circuit that extends from a length from the scan head 602 to the integrated circuit 636. As can be seen in FIG. 10, the interposer 638 is bent at multiple locations along the length of the interposer 638. The interposer 538 includes opposite sides 658 and 660.

The interposer 638 is electrically connected to the array of acoustic elements 614 and/or the integrated circuit 636 using an electrically conductive adhesive (not shown) that is anisotropically conductive. The interposer 638 may be electrically connected to the array of acoustic elements 614 using an anisotropic electrically conductive adhesive in a manner substantially similar to that described and illustrated herein with respect to the connection between the interposer 38 and the array of acoustic elements 14 using the electrically conductive adhesive 40 (shown in FIG. 3). For example, the electrically conductive adhesive may include a layer (not shown) that extends between the array of acoustic elements 614 and either of the sides 658 or 660 of the interposer 638.

The interposer 638 may be electrically connected to the integrated circuit 636 using an anisotropic electrically conductive adhesive in a manner substantially similar to that described and illustrated herein with respect to the connection between the interposer 38 and the integrated circuit 36 using the electrically conductive adhesive 40 (shown in FIG. 3). For example, the electrically conductive adhesive may include a layer (not shown) that extends between the integrated circuit 636 and either of the sides 658 or 660 of the interposer 638.

Various embodiments provide a connection between various components of an ultrasound transducer using an electrically conductive adhesive, wherein the connection has a predetermined mechanical strength and a predetermined electrical conductivity. The mechanical connection may have a predetermined mechanical strength that facilitates preventing the connection from being severed, for example during operation and/or transport of the ultrasound transducer. The electrically conductive adhesive may have a relatively fast curing time. The various embodiments may provide an ultrasound transducer that can be manufactured in less time and/or that is more robust to temperature changes.

It should be noted that although the various embodiments may be described in connection with an ultrasound system, the methods and systems are not limited to ultrasound imaging or a particular configuration thereof. The various embodiments may be implemented in connection with different types of imaging systems, including, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound transducer comprising:
an array of acoustic elements;
an integrated circuit;
an interposer comprising conductive elements that electrically connect the array of acoustic elements to the integrated circuit;
an electrically conductive adhesive that is engaged with the conductive elements of the interposer to electrically connect the interposer to at least one of the integrated circuit or the array of acoustic elements, wherein the electrically conductive adhesive is anisotropically conductive; and
wherein the integrated circuit comprises electrical contacts, the electrically conductive adhesive being engaged with the conductive elements of the interposer and being engaged with the electrical contacts of the integrated circuit such that the interposer and the array of acoustic elements are electrically connected together through the electrically conductive adhesive.

2. The ultrasound transducer of claim 1, wherein the interposer comprises a side that faces the integrated circuit or the array of acoustic elements, the electrically conductive adhesive being anisotropically conductive such that the electrically conductive adhesive only conducts electrical energy along an axis that extends approximately perpendicular to the side of the interposer.

3. The ultrasound transducer of claim 1, wherein the electrically conductive adhesive comprises a first electrically conductive adhesive layer that electrically connects the conductive elements of the interposer to the integrated circuit and a second electrically conductive layer that electrically connects the conductive elements of the interposer to the array of acoustic elements, each of the first and second electrically conductive layers comprising at least one of an electrically conductive film or an electrically conductive paste.

4. The ultrasound transducer of claim 1, wherein the array of acoustic elements, the interposer, and the integrated circuit are arranged in a stack, the interposer extending between the integrated circuit and the array of acoustic elements within the stack.

5. The ultrasound transducer of claim 1, wherein the array of acoustic elements comprises electrical contacts, the electrically conductive adhesive being engaged with the conductive elements of the interposer and being engaged with the electrical contacts of the array of acoustic elements such that the interposer and the array of acoustic elements are electrically connected together through the electrically conductive adhesive.

6. The ultrasound transducer of claim 1, wherein the electrically conductive adhesive is configured to conduct both the transmission and reception of ultrasound signals.

7. The ultrasound transducer of claim 1, wherein the interposer comprises a side that faces the integrated circuit or the array of acoustic elements, the electrically conductive adhesive being anisotropically conductive such that the electrically conductive adhesive does not conduct electrical energy along an axis that extends approximately parallel to the side of the interposer.

8. The ultrasound transducer of claim 1, wherein the electrical conductive adhesive comprises a combination of an electrically conductive film and an electrically conductive paste.

9. The ultrasound transducer of claim 1, wherein the interposer comprises at least one of a flex circuit or a flex cable.

10. The ultrasound transducer of claim 1, wherein the conductive elements of the interposer comprise at least one of an electrical via, an electrical trace, or an electrical contact pad.

11. The ultrasound transducer of claim 1, wherein the array of acoustic elements is a two-dimensional (2D) array.

12. The ultrasound transducer of claim 1, further comprising a non-electrically conductive adhesive that mechanically connects the interposer to at least one of the integrated circuit or the array of acoustic elements.

13. The ultrasound transducer of claim 1, wherein the electrically conductive adhesive comprises a first electrically conductive adhesive layer that electrically connects the conductive elements of the interposer to the integrated circuit and a second electrically conductive layer that electrically connects the conductive elements of the interposer to the array of acoustic elements, wherein the first and second electrically conductive adhesive layers are each anisotropically conductive.

14. An ultrasound transducer comprising:
an array of acoustic elements;
an integrated circuit;
a first interposer comprising first conductive elements;
a second interposer comprising second conductive elements; and
an electrically conductive adhesive that is anisotropically conductive, the electrically conductive adhesive comprising:
a first electrically conductive adhesive layer that is engaged with the first conductive elements of the first interposer such that the first electrically conductive adhesive layer electrically connects the first conductive elements to the acoustic elements;
a second electrically conductive adhesive layer that is engaged with the first conductive elements of the first interposer and the second conductive elements of the second interposer such that the second electrically conductive adhesive layer electrically connects the first and second conductive elements together; and
a third electrically conductive adhesive layer that is engaged with the second conductive elements of the second interposer such that the third electrically conductive adhesive layer electrically connects the second conductive elements to the integrated circuit.

15. An ultrasound transducer comprising:
an array of acoustic elements comprising electrical contacts;
an integrated circuit comprising electrical contacts;
a first electrically conductive adhesive layer;
a second electrically conductive adhesive layer;
wherein the first electrically conductive adhesive layer is engaged with the electrical contacts of the array of acoustic elements and is engaged with the second electrical conductive adhesive layer, such that the electrical contacts of the array of acoustic elements electrically connects to the second electrically conductive adhesive layer; and
wherein the second electrically conductive adhesive layer is engaged with the electrical contacts of the integrated circuit and is engaged with the first electrically conductive adhesive layer, such that the first electrically conductive adhesive layer electrically connects to the electrical contacts of the integrated circuit.

* * * * *